(12) United States Patent
Astier et al.

(10) Patent No.: US 10,048,204 B2
(45) Date of Patent: *Aug. 14, 2018

(54) NANOPILLAR MICROFLUIDIC DEVICES AND METHODS OF USE THEREOF

(71) Applicant: INTERNATIONAL BUSINESS MACHINES CORPORATION, Armonk, NY (US)

(72) Inventors: Yann Astier, Irvington, NY (US); Huan Hu, Yorktown Heights, NY (US); Ning Li, White Plains, NY (US); Devendra K. Sadana, Pleasantville, NY (US); Joshua T. Smith, Croton on Hudson, NY (US); William T. Spratt, Ossining, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/602,634

(22) Filed: May 23, 2017

(65) Prior Publication Data

US 2017/0254753 A1    Sep. 7, 2017

Related U.S. Application Data

(63) Continuation of application No. 14/942,072, filed on Nov. 16, 2015, now Pat. No. 9,719,926.

(51) Int. Cl.
*G01N 31/22* (2006.01)
*G01N 21/64* (2006.01)
(Continued)

(52) U.S. Cl.
CPC ..... *G01N 21/6428* (2013.01); *H01L 31/0288* (2013.01); *H01L 31/035227* (2013.01); *H01L 31/173* (2013.01); *H01L 33/06* (2013.01); *H01L 33/24* (2013.01); *H01L 33/30* (2013.01); *H01L 33/32* (2013.01); *H01L 33/44* (2013.01); *G01N 2021/6439* (2013.01); *G01N 2201/062* (2013.01)

(58) Field of Classification Search
None
See application file for complete search history.

(56) References Cited

U.S. PATENT DOCUMENTS 6,962,823 B2 * 11/2005 Empedocles ......... B81C 99/008
                                                          438/105
2004/0197843 A1 * 10/2004 Chou ................... C12Q 1/6869
                                                          435/7.92

(Continued)

OTHER PUBLICATIONS

List of IBM Patents or Patent Applications Treated As Related; (Appendix P), Date Filed May 23, 2017; 2 pages.

*Primary Examiner* — Jill A Warden
*Assistant Examiner* — Brittany I Fisher
(74) *Attorney, Agent, or Firm* — Cantor Colburn LLP; Louis Percello

(57) ABSTRACT

Described herein are microfluidic devices and methods of detecting an analyte in a sample that includes flowing the sample though a microfluidic device, wherein the presence of the analyte is detected directly from the microfluidic device without the use of an external detector at an outlet of the microfluidic device. In a more specific aspect, detection is performed by incorporating functional nanopillars, such as detector nanopillars and/or light source nanopillars, into a microchannel of a microfluidic device.

18 Claims, 5 Drawing Sheets

(51) Int. Cl.
    *H01L 33/24*     (2010.01)
    *H01L 33/06*     (2010.01)
    *H01L 33/30*     (2010.01)
    *H01L 33/32*     (2010.01)
    *H01L 31/0352*     (2006.01)
    *H01L 31/0288*     (2006.01)
    *H01L 31/173*     (2006.01)
    *H01L 33/44*     (2010.01)

(56) References Cited

U.S. PATENT DOCUMENTS

| | | | |
|---|---|---|---|
| 2008/0081326 A1* | 4/2008 | Amano | B82Y 15/00 435/5 |
| 2010/0033561 A1* | 2/2010 | Hersee | G02B 21/002 348/80 |
| 2011/0315988 A1* | 12/2011 | Yu | H01L 27/14 257/52 |
| 2012/0013515 A1* | 1/2012 | Berejik | H01Q 1/125 343/766 |
| 2013/0200334 A1* | 8/2013 | Zhang | H01L 33/04 257/13 |
| 2013/0307029 A1* | 11/2013 | Xu | G01N 27/4145 257/253 |
| 2014/0030788 A1* | 1/2014 | Chen | B01L 3/502707 435/177 |
| 2014/0239327 A1* | 8/2014 | Konsek | B82Y 20/00 257/98 |
| 2015/0136601 A1* | 5/2015 | Austin | G01N 27/44791 204/451 |
| 2017/0138858 A1 | 5/2017 | Astier et al. | |

\* cited by examiner

Single pillar pixels

Multi pillar pixels

Only pillars near the outlet are functional

NANOPILLAR MICROFLUIDIC DEVICES AND METHODS OF USE THEREOF

CROSS-REFERENCE TO RELATED APPLICATIONS AND DOMESTIC CLAIM

This application is a continuation of and claims priority from U.S. patent application Ser. No. 14/942,072 filed on Nov. 16, 2015, entitled "NANOPILLAR MICROFLUIDIC DEVICES AND METHODS OF USE THEREOF", the entire contents of which are incorporated herein by reference.

BACKGROUND

The present invention relates to surfaces containing nanopillars, and more specifically, to nanopillar microfluidic devices useful as biosensors.

Microfluidic devices are used to implement separation techniques, such as the separation and identification of proteins in proteomics applications. In the case of charged biomolecules such as proteins, microfluidic devices containing an electrophoresis separation channel such as a microchip capillary electrophoresis (μ-CE) channel, can be used to separate analytes in a small volume fluid sample. Fluorescence detection, for example, may be used post-separation to monitor the separated analytes. The analyte stream may be fed into an electrical, optical or magnetic detection device, for example, depending upon the labeling scheme that is employed. What is needed are microfluidic devices that allow for improved detection of separated analytes.

SUMMARY

According to an embodiment of the present invention, a microfluidic device comprises at least one microchannel, the microchannel having a bottom opposite a top and two opposite side walls, wherein the microchannel comprises a plurality of functional nanopillars, wherein the functional nanopillars comprise a p-n junction semiconductor material, and wherein the functional nanopillars comprise detector nanopillars, light source nanopillars, or both.

According to another embodiment, a method of detecting an analyte in a sample comprises flowing the sample though a microfluidic device, wherein the presence of the analyte is detected directly from the microfluidic device without the use of an external detector at an outlet of the microfluidic device.

DETAILED DESCRIPTION

Figure 1:
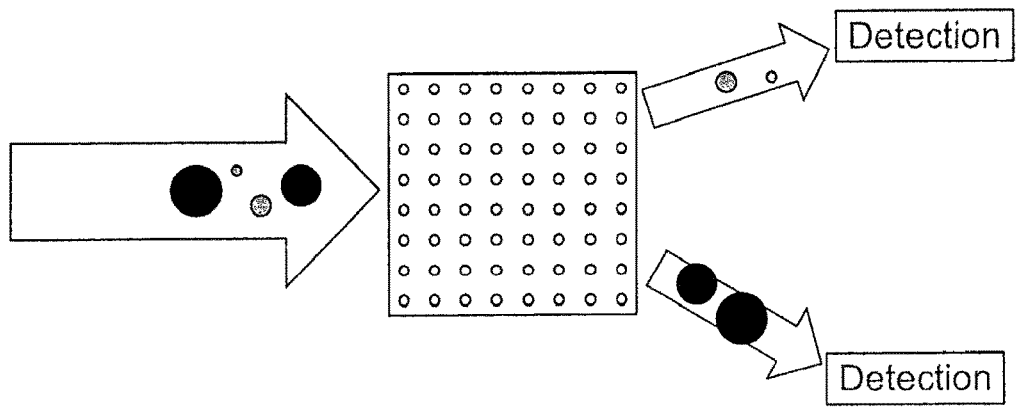
FIG. 1 shows a prior art nanopillar microfluidic device.
Figure 2:
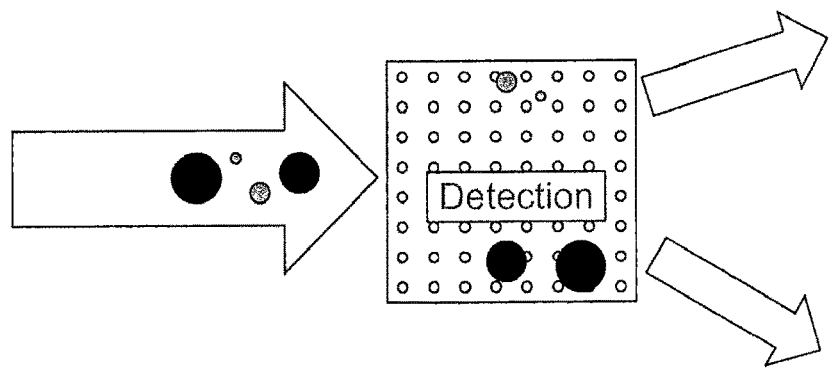
FIG. 2 shows a device of the present disclosure in which detection is integrated into the microfluidic device.

With reference now to FIG. 1, a prior art nanopillar microfluidic device is shown in which analytes are separated and, after separation, detection of the sorted fractions is performed by sending the sorted fractions to a detection device that is external to the microfluidic device. FIG. 2 illustrates a device according to the present disclosure in which detection is performed directly on the microfluidic device, that is, the detection is integrated into the microfluidic device. According to an embodiment, a method of detecting an analyte in a sample comprises flowing the sample though a microfluidic device, wherein the presence of the analyte is detected directly from the microfluidic device without the use of an external detector at an outlet of the microfluidic device. In a more specific aspect, detection is performed by incorporating functional nanopillars, such as detector nanopillars and/or light source nanopillars as described herein, into a microchannel of a microfluidic device. For fluorescence detection of an analyte, for example, both detectors and a light source are integrated into the device. The device disclosed herein provides compact integration of analyte sorting and detection.

As used herein a "nanopillar" is a three-dimensional structure having an elongated, vertical pillar structure and a diameter of up to about 2 μm, such as 20 to 200 nm, for example. Nanopillars can have a length to width ratio of 50:1, 25 to 2 or 15 to 3, or 3:1, for example. Fabrication of nanopillars can be performed using bottom-up self-assembly techniques, or top-down techniques such as lithography and etching as are known in the art. While the term "nanopillar" is generally used herein, the term nanopillar also includes micropillars, which are pillar structure having diameters in the micrometer size range rather than the nanometer size range.

As used herein, a "microfluidic device" is a device suitable for processing small volumes of fluid containing analytes, such as nanoliter and picoliter volumes of fluid. In general, microfluidic devices have dimensions of millimeters to nanometers, and comprise one or more microchannels, as well as inlet and outlet ports that allow fluids to pass into and out of the microfluidic device. A microfluidic chip, for example, is a microfluidic device into which a network of microchannels has been molded or patterned.

As used herein, a "microchannel" is a channel of a microfluidic device which provides a flow path for an analyte. In general, microchannels have at least one dimension less than 1 mm.

As used herein, the term "analyte" refers to a compound, molecule, substance, or chemical constituent that is undergoing analysis or sought to be detected. It is not intended that the present disclosure be limited to a particular analyte. Representative analytes include ions, saccharides, proteins, nucleic acids, cells, and cellular organelles, e.g., exosomes. Analytes may be labeled, e.g., fluorescently labeled, using methods known in the art.

In one aspect, described herein is a microfluidic device comprising at least one microchannel, the microchannel having a bottom opposite a top and two opposite side walls, wherein the microchannel comprises a plurality of functional nanopillars, wherein the functional nanopillars comprise a p-n junction semiconductor material. The functional nanopillars include detector nanopillars, light source nanopillars, or both.

A "detector nanopillar" is a nanopillar that can detect the presence of an analyte, such as a fluorescently labeled polypeptide, in a sample. In one aspect, excitation light produced by an LED substrate or a light source nanopillar, produces a fluorescent signal from a fluorescently labeled analyte, and the fluorescence from the analyte is detected by the detector nanopillar. When the fluorescent signal is detected by the detector nanopillar, it is converted to an electrical signal which can then be outputted from the device.

Exemplary materials for a detector nanopillar include intrinsic (undoped), n-doped (e.g., with phosphorus) and p-doped (e.g., with boron) silicon, as well as conductive polymers, and combinations of the foregoing. A detector nanopillar is a p-n junction semiconductor and thus comprises n-doped and/or p-doped silicon, for example. Varying the levels of n-doping and p-doping in the detector nanopillars can be used to adjust the electrical properties of the device, for example, to adjust the wavelengths of light detected by the detector nanopillars.

Exemplary organic conductive polymers include poly(acetylene)s, poly(pyrrole)s, poly(thiophene)s, polyanilines, polythiophenes, poly(p-phenylene sulfide), poly(para-phenylene vinylene)s (PPV) and PPV derivatives, poly(3-alkylthiophenes), polyindole, polypyrene, polycarbazole, polyazulene, polyazepine, poly(fluorene)s, and polynaphthalene. Other examples include polyaniline, polyaniline derivatives, polythiophene, polythiophene derivatives, polypyrrole, polypyrrole derivatives, polythianaphthene, polythianaphthane derivatives, polyparaphenylene, polyparaphenylene derivatives, polyacetylene, polyacetylene derivatives, polydiacethylene, polydiacetylene derivatives, polyparaphenylenevinylene, polyparaphenylenevinylene derivatives, polynaphthalene, and polynaphthalene derivatives, polyisothianaphthene (PITN), polyheteroarylenvinylene (ParV), in which the heteroarylene group can be, e.g., thiophene, furan or pyrrol, polyphenylene-sulphide (PPS), polyperinaphthalene (PPN), polyphthalocyanine (PPhc) etc., and their derivatives, copolymers thereof and mixtures thereof. The conductive polymers can be subjected to p-doping or n-doping to be transformed into a conductive polymer. The semiconductor polymer may be doped chemically, or electrochemically. The substance used for the doping is not particularly limited; generally, a substance capable of accepting an electron pair, such as a Lewis acid, is used. Examples include hydrochloric acid, sulfuric acid, organic sulfonic acid derivatives such as parasulfonic acid, polystyrenesulfonic acid, alkylbenzenesulfonic acid, camphorsulfonic acid, alkylsulfonic acid, sulfosalycilic acid, etc., ferric chloride, copper chloride, and iron sulfate.

A "light source nanopillar" is, for example, an LED that provides an excitation source for labeled analytes that are to be separated and/or detected. A light source nanopillar comprises intrinsic, n-doped or p-doped gallium arsenide (GaAs), gallium nitride (GaN) or indium gallium nitride (InGaN), or a combination thereof, for example. A light source nanopillar is a p-n junction semiconductor and thus comprises n-doped and/or p-doped GaAs, for example. More specifically, a light source nanopillar comprises n-doped or p-doped gallium arsenide (GaAs), gallium nitride (GaN), indium gallium nitride (InGaN), or a combination thereof. Varying the levels of n-doping and p-doping in the light source nanopillars can be used to adjust the electrical properties of the device, for example, the wavelength of light provided by the light source nanopillars. In one aspect, the light source nanopillar is an LED nanopillar. GaN based LEDs, for example, can emit blue light, ultraviolet (UV) light, or both, for example. N-dopants for the light source nanopillars include silicon, while p-dopants for the light source nanopillars include zinc, beryllium and magnesium.

In one aspect, the detector or light source nanopillars are coated with a thin interference coating or an organic dye to provide wavelength filtering. The coating can be used to separate the fluorescence wavelengths of the molecules with the LED pump light wavelength. Exemplary coatings include multilayer dielectric coatings.

In certain aspects, the microchannel, like the detector nanopillars and the light source nanopillars, comprises a semiconductive material such as n-doped or p-doped silicon, n-doped or p-doped silicon dioxide, n-doped or p-doped gallium arsenide. The microchannel can also comprise a conductive polymer as described above for the detector nanopillars. Combinations of the foregoing materials may also be used.

In the case of fluorescence detection of analytes, an LED can be incorporated in the form of light source nanopillars, in the substrate, or in the top of the microchannel, as illustrated in FIGS. 3-7. The excitation light emitted by the LED provides fluorescence of the fluorescently labeled analyte, and the fluorescence is detected by interaction of the emitted fluorescence with the detector nanopillars. In certain aspects, the nanopillar detector can detect color due to a quantum confinement effect. Specifically, by integrating different sizes of nanopillars, the different sizes of nanopillars can absorb light at different wavelengths. For example, the smaller the nanopillar, the larger the energy gap, and the shorter the wavelength of light to be detected.

Figure 3:
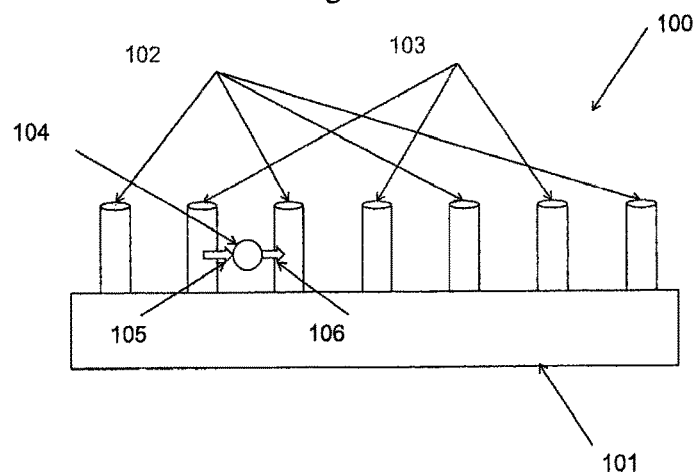
FIG. 3 shows an embodiment of a microfluidic device of the present disclosure, including intermingled detector and light source nanopillars.

As shown in FIG. 3, in one aspect a microchannel (100) comprises both detector nanopillars (102) and light source nanopillars (103) disposed on a substrate (101), for example intermingled detector and light source nanopillars. In this embodiment, for example, the light source pillars produce wavelengths of light (105) that excite fluorescence in fluorescently labeled analytes (104), and the fluorescence (106) is then detected by the nanopillars.

Figure 4:
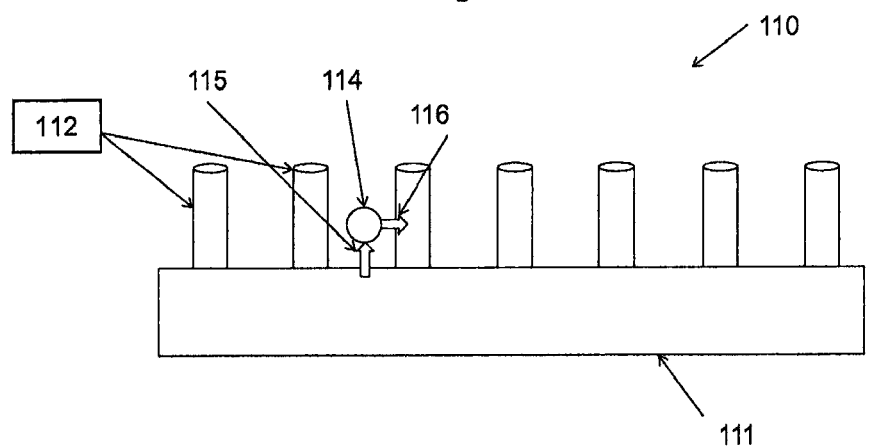
FIG. 4 shows an embodiment of a microfluidic device of the present disclosure including detector nanopillars and a substrate containing an LED light source.

As shown in FIG. 4, in another embodiment, a microchannel (110) comprises detector nanopillars (112), disposed on a substrate (111), wherein the substrate comprises embedded LEDs. In this embodiment, for example, the substrate produces wavelengths of light (115) that excite fluorescence (116) in fluorescently labeled analytes (114). In an alternative embodiment, the substrate comprises a detector and the microchannel comprises light source pillars.

Figure 5:
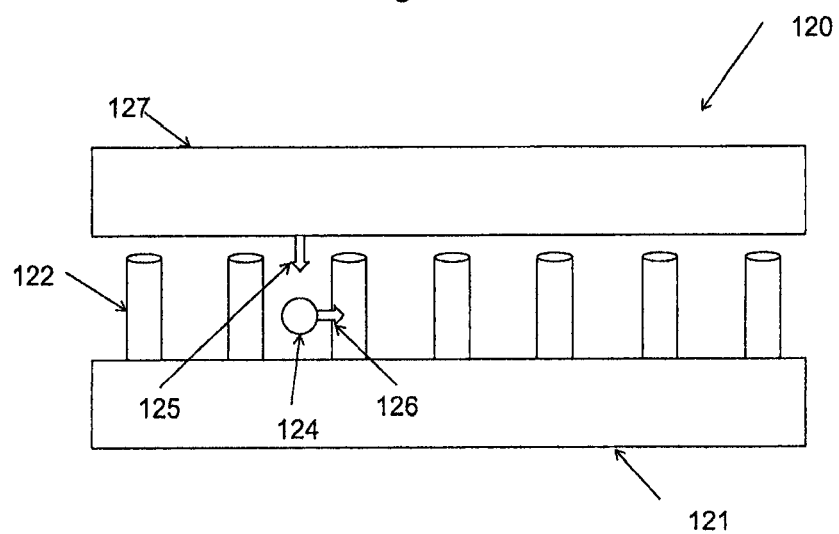
FIG. 5 shows an embodiment of a microfluidic device of the present disclosure including detector nanopillars and a device bonded to top of the microchannel which contains LEDs.

As shown in FIG. 5, in another embodiment, a microchannel (120) comprises detector nanopillars (122) and disposed on a substrate (121), wherein a device comprising LEDs (127) is bonded to the top of the microchannel, both sealing the microchannel and providing a light source. In this embodiment, for example, the device comprising LEDs produces wavelengths of light (125) that that excite fluorescence (126) in fluorescently labeled analytes (124).

Figure 6:
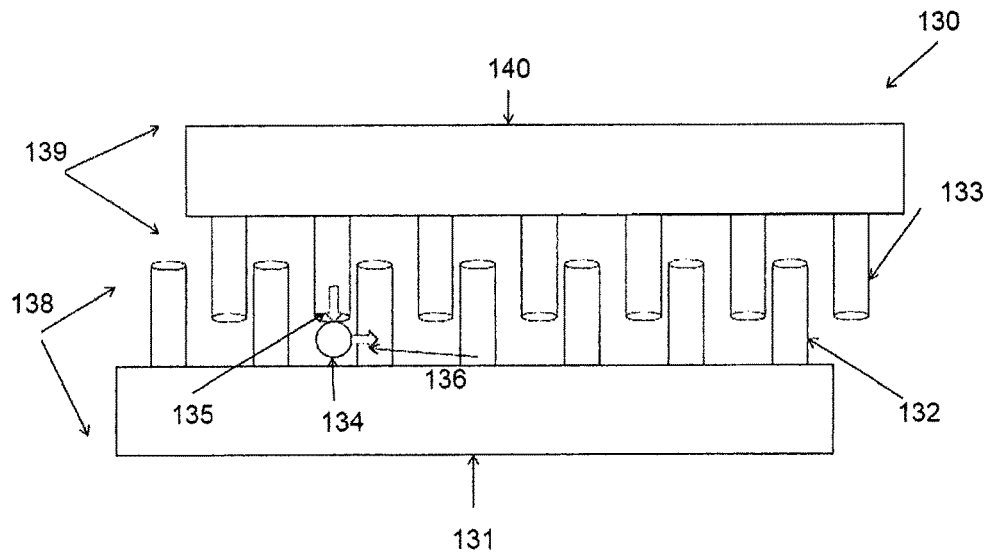
FIG. 6 shows an embodiment of a microfluidic device of the present disclosure including a bottom comprising detector nanopillars and a top comprising light source nanopillars.

As shown in FIG. 6, a microchannel (130) comprises a bottom (138) comprising detector nanopillars (132) disposed on a bottom substrate (131), and a top (139) opposed to the bottom, the top comprising light source nanopillars (133) disposed on a top substrate (140). In this embodiment, for example, the light source nanopillars produce wavelengths of light (135) that that excites fluorescence (136) in fluorescently labeled analytes (134).

Figure 7:
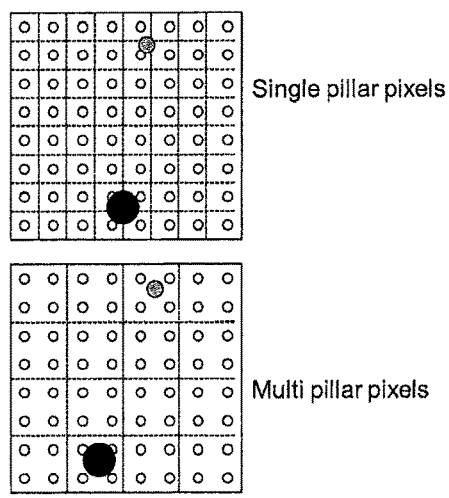
FIG. 7 shows embodiments of an array of detector nanopillars.

As shown in FIG. 7, detector nanopillars can be arranged in the form of an array, wherein the detector pillars are addressable either individually or in groups. In this embodiment, the nanopillars or groups of nanopillars are addressable (e.g., like in a CCD array), and this analytes can be tracked as they navigate the array (e.g., using a microscope with a CCD camera).

Figure 8:
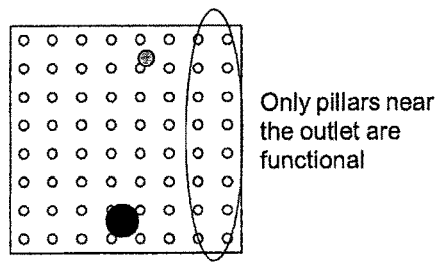
FIG. 8 shows an embodiment, wherein functional nanopillars are clustered near the outlet of the micro channel.

As shown in FIG. 8, in certain embodiments, the microchannel comprises an inlet and an outlet, wherein analytes flow from the inlet to the outlet. In this embodiment, the detector and/or light source nanopillars may be clustered near the outlet to reduce complexity and costs. This scheme can be applied to any of the devices of FIGS. 3-7, for example.

Figure 9:
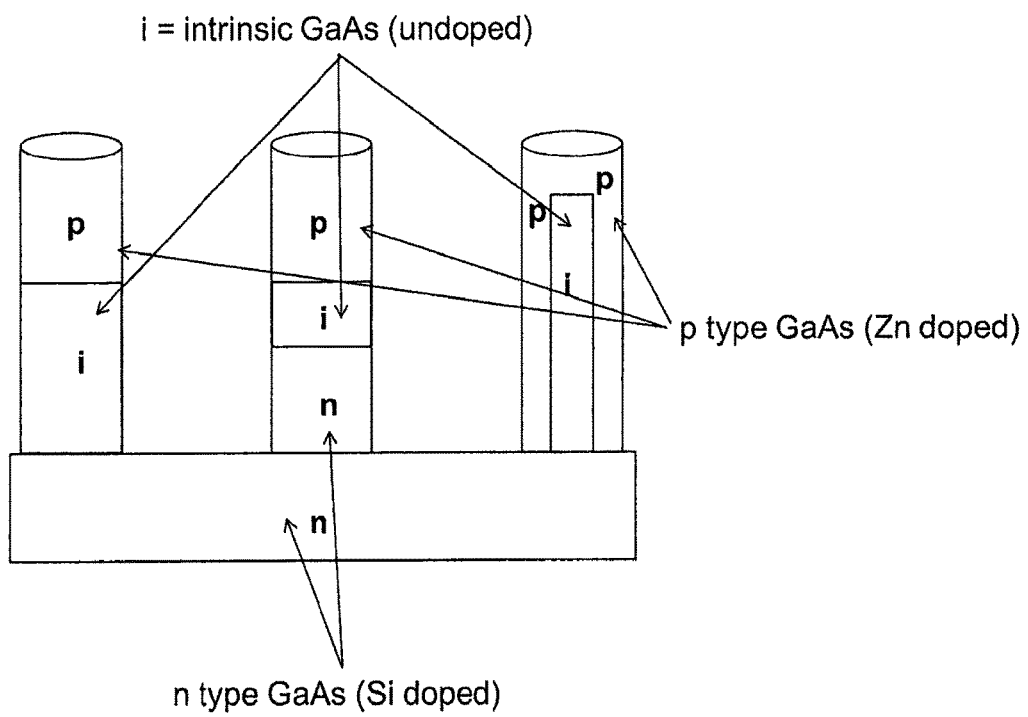
FIG. 9 shows fabrication possibilities for light source nanopillars.

FIG. 9 shows fabrication possibilities for light source nanopillars. The light source nanopillars may comprise intrinsic GaAs, for example, in addition to n-doped and/or p-doped GaAs, so long as the resulting nanopillar is a p-n junction semiconductor. In addition, the substrate may comprise Si, GaAs, InP, GaN, sapphire, and the like.

Figure 10:
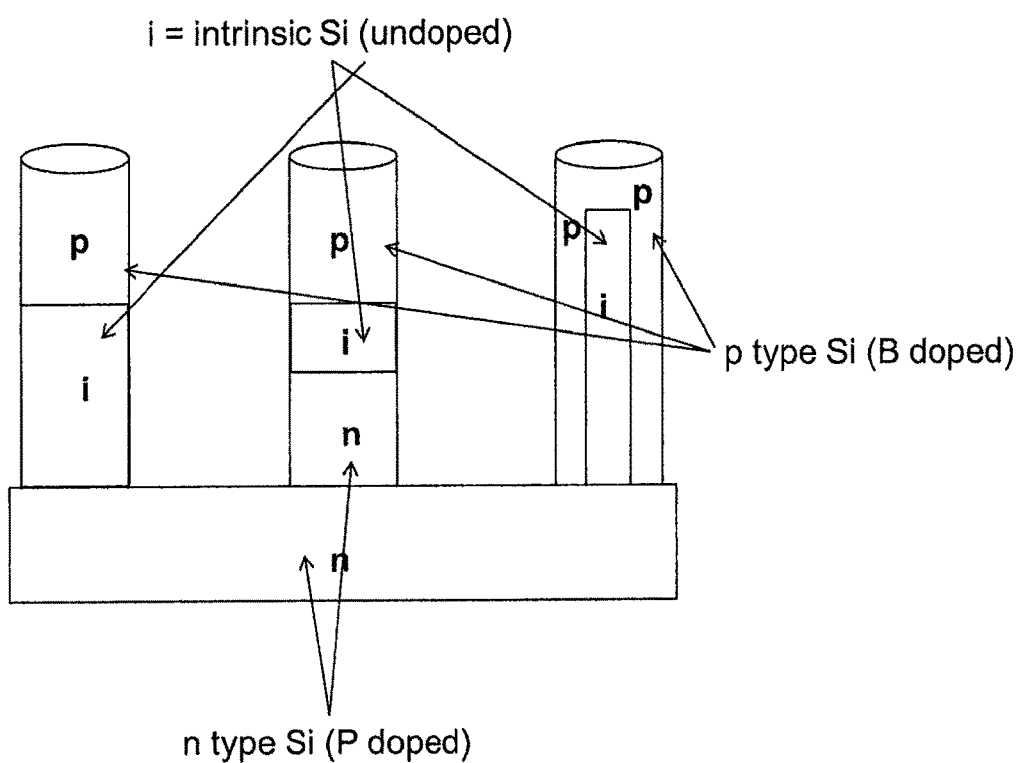
FIG. 10 shows fabrication possibilities for detector nanopillars.

FIG. 10 shows fabrication possibilities for detector nanopillars. The detector nanopillars may comprise intrinsic Si, for example, in addition to n-doped and/or p-doped Si, so long as the resulting nanopillar is a p-n junction semiconductor. In addition, the substrate may comprise Si, GaAs, InP, GaN, sapphire, and the like.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A microfluidic device comprising:
at least one microchannel, the microchannel having a bottom opposite a top and two opposite side walls, wherein the microchannel comprises a plurality of integrated functional nanopillars, wherein the functional nanopillars comprise a p-n junction semiconductor material, and further wherein the functional nanopillars comprise detector nanopillars, wherein the detector nanopillars are coated with a thin interference coating or an organic dye.

2. The microfluidic device of claim 1, wherein the detector nanopillars comprise n-doped silicon, p-doped silicon, a conductive polymer, or a combination thereof.

3. The microfluidic device of claim 1, wherein the functional nanopillars further comprise light source nanopillars.

4. The microfluidic device of claim 3, wherein the light source nanopillars comprise n-doped or p-doped gallium arsenide, n-doped or p-doped gallium nitride, n-doped or p-doped indium gallium nitride, or a combination thereof.

5. The microfluidic device of claim 3, wherein the light source nanopillars produce wavelengths of light that excite fluorescently labeled analytes.

6. The microfluidic device of claim 1, wherein the detector nanopillars are coated with a multilayer dielectric coating.

7. The microfluidic device of claim 1, comprising a fluorescent analyte.

8. The microfluidic device of claim 1, wherein the detector nanopillars are present in the microchannel, and wherein the detector nanopillars are disposed on a substrate comprising embedded LEDs.

9. The microfluidic device of claim 8, comprising a fluorescently labeled analyte excited by the embedded LEDs.

10. The microfluidic device of claim 1, further comprising LEDs bonded to the top of the device.

11. The microfluidic device of claim 10, comprising a fluorescently labeled analyte excited by the LEDs bonded to the top of the device.

12. The microfluidic device of claim 1, wherein the detector nanopillars are in the form of an array.

13. The microfluidic device of claim 12, wherein the detector nanopillars are addressable individually.

14. The microfluidic device of claim 12, wherein the detector nanopillars are addressable in groups.

15. The microfluidic device of claim 1, wherein the microchannel comprises an inlet and an outlet, wherein analytes flow from the inlet to the outlet, and wherein the functional nanopillars are clustered near the outlet.

16. The microfluidic device of claim 1, wherein at least some of the plurality of integrated functional nanopillars have different dimensions and absorb light at different wavelengths.

17. A microfluidic device comprising:
at least one microchannel, the microchannel having a bottom opposite a top and two opposite side walls, wherein the microchannel comprises a plurality of integrated functional nanopillars, wherein the functional nanopillars comprise a p-n junction semiconductor material, and further wherein the functional nanopillars comprise detector nanopillars, wherein the microchannel comprises n-doped or p-doped silicon, n-doped or p-doped silicon dioxide, n-doped or p-doped gallium arsenide, a conductive polymer, or a combination thereof.

18. A microfluidic device comprising:
at least one microchannel, the microchannel having a bottom opposite a top and two opposite side walls, wherein the microchannel comprises a plurality of integrated functional nanopillars, wherein the functional nanopillars comprise a p-n junction semiconductor material formed on a substrate, and further wherein the functional nanopillars comprise detector nanopillars, wherein the detector nanopillars comprise intrinsic silicon, n-doped silicon, p-doped silicon, or both, wherein the substrate comprises Si, GaAs, InP, GaN, or sapphire.

* * * * *